United States Patent [19]

Douthart et al.

[11] 4,400,375

[45] Aug. 23, 1983

[54] TOBRAMYCIN-DOUBLE STRANDED RNA COMPLEX SUITABLE FOR INDUCING INTERFERON

[75] Inventors: Richard J. Douthart, Martinsville; Walter J. Kleinschmidt; Richard M. Schultz, both of Indianapolis, all of Ind.

[73] Assignee: Eli Lilly and Company, Indianapolis, Ind.

[21] Appl. No.: 324,241

[22] Filed: Nov. 23, 1981

[51] Int. Cl.$^3$ ...................... A61K 45/04; C07H 21/02
[52] U.S. Cl. ...................................... 424/85; 424/180; 536/16.8; 536/28; 536/29
[58] Field of Search ................ 536/28, 29, 17 R, 16.8; 424/85, 180

[56] References Cited

U.S. PATENT DOCUMENTS

| | | | |
|---|---|---|---|
| 3,679,654 | 7/1972 | Mass | 260/112.5 |
| 3,821,193 | 6/1974 | Fare et al. | 536/28 |
| 3,845,033 | 10/1974 | Harnden | 260/211.5 R |
| 4,130,641 | 12/1978 | Ts'o et al. | 536/28 |
| 4,349,538 | 9/1982 | Levy | 425/85 |

OTHER PUBLICATIONS

Nordlund et al., *Proc. Soc. Exp. Biol. and Med.*, 133, 439 (1970).
Houston, W. E. et al., *Infection and Immunity* 14, 318–319 (1976).
Billiau, A. et al., *Ann. N.Y. Acad. Sci.*, 173, 657–667, (1970).
Lampson, G. P. et al., *Proc. Soc. Exp. Biol. and Med.*, 132, 212–218 (1969).
Levy, H. B. et al., *Proc. Nat. Acad. Sci.*, 62, 357–361 (1969).
Zeleznick, L. D. et al., *Proc. Soc. Exp. Biol. Med.*, 130, 126–128 (1969).
Gelboin, H. V. et al., *Science*, 167, 205–207 (1970).

*Primary Examiner*—Nicky Chan
*Attorney, Agent, or Firm*—William C. Martens; Arthur R. Whale

[57] ABSTRACT

A complex is described which is useful in inducing interferon production, in activating peritoneal macrophages, and in inhibiting the proliferation and migration of tumor cells, which complex comprises natural or synthetic double stranded RNA and tobramycin.

10 Claims, No Drawings

TOBRAMYCIN-DOUBLE STRANDED RNA COMPLEX SUITABLE FOR INDUCING INTERFERON

BACKGROUND OF THE INVENTION

Interferon is a naturally-occurring antiviral protein produced by most cells upon stimulation by virus infection or other substances recognized as interferon "inducers". The potential of interferon as a broad spectrum antiviral and/or anti-tumor agent has long been recognized.

Double stranded RNA (dsRNA), whether of synthetic, e.g., polyriboinosinic-polyribocytidilic acid (poly I:poly C), or natural origin, is recognized as an excellent inducer of interferon. Unfortunately, the usefulness of natural or synthetic dsRNA is greatly limited due to its rapid degradation by nucleases present in the sera of various animal species, particularly primates. More significantly, the enzymatic degradation of dsRNA is especially apparent in human serum; see, for example, R. J. Douthart and S. G. Burgett, *Biochem. and Biophys. Res. Comm.* 84 (1978), 809–815.

It is essential, therefore, if dsRNA is to be useful as an inducer of interferon in primates, in particular, humans, that its rapid enzymatic degradation be prevented or substantially diminished.

Attempts have been made to promote the interferon-inducing activity of dsRNA, for example, by stabilizing it against enzymatic degradation by a variety of approaches.

W. E. Houston, C. L. Crabbs, E. L. Stephen, and H. B. Levy, *Infection and Immunity* 14, (1976), 318–319, report stabilization of poly I:poly C against enzymatic degradation using poly-L-lysine and carboxymethylcellulose.

A. Billiau, C. E. Buckler, F. Dianzani, C. Uhlendorf, and S. Baron, *Ann. N.Y. Acad. Sci.*, 173 (1970) 657–667, report that stimulation of the interferon mechanism in tissue culture by poly I:poly C can be enhanced by addition of substances such as neomycin, streptomycin, diethylaminoethyl dextran (DEAE-dextran), methylated albumin, protamine, histone, and colistin. Neomycin and protamine, each when administered to mice in conjunction with poly I:poly C, were shown to have no effect on the yield of circulating interferon. DEAE-dextran, on the other hand, showed a definite enhancement of the interferon response from separately-administered poly I:poly C.

G. P. Lampson, A. A. Tytell, A. K. Field, M. M. Nemes, and M. R. Hilleman, *Proc. Soc. Exp. Biol. and Med.*, 132, (1969) 212–218, measured the effect of several polyamines used in conjunction with poly I:poly C. Of ten polyamines tested, five demonstrated some effect toward the stabilization of poly I:poly C in the presence of RNase. Most of the testing was carried out using neomycin with the stated conclusion that the "effect of neomycin was entirely limited to in vitro activity in one particular kind of cell and showed no potential for practical utilization in human and animal application either in potentiation of poly I:C activity or in reduction of its toxicity." (page 217).

J. J. Nordlund, S. M. Wolff, and H. B. Levy, *Proc. Soc. Exp. Biol. and Med.*, 133, (1970) 439–444, suggest that human plasma is capable of rapid enzymatic degradation of poly I:poly C in contrast, e.g., to rabbit serum. They further report the elimination by neomycin of the destructive capacity of dilute (15%) human plasma.

A new complex of natural or synthetic dsRNA recently has been discovered. This complex, a combination of dsRNA and tobramycin has been shown to have the highly advantageous properties of (1) ability to induce interferon; (2) stability in the presence of human plasma containing dsRNase; (3) ability to activate peritoneal macrophages; and (4) enhancement of the activity of dsRNA against tumor systems, including highly refractory tumors such as the Madison lung tumor, even in species having low levels of dsRNase in which there is no demonstrable difference in peak interferon titers produced by dsRNA alone and the tobramycin:dsRNA complex.

SUMMARY OF THE INVENTION

Therefore, this invention is directed to an interferon-inducing and anti-tumor composition comprising a complex of (a) natural or synthetic double stranded RNA and (b) tobramycin in a molar ratio of tobramycin to double stranded RNA phosphorus of at least about 1:1.

Another aspect of this invention is a pharmaceutical composition comprising in combination with a pharmaceutically acceptable carrier a complex of (a) natural or synthetic double stranded RNA and (b) tobramycin in a molar ratio of tobramycin to double stranded RNA phosphorus of at least about 1:1.

A further aspect of this invention is a method for retarding degradation of natural or synthetic double stranded RNA caused by ribonucleases present in human serum, which comprises combining said double stranded RNA with tobramycin in an amount of at least about 1 mole tobramycin per gram atom of phosphorus present in the double stranded RNA.

DETAILED DESCRIPTION OF THE INVENTION

As noted, this invention provides an antitumor and interferon-inducing composition containing double stranded ribonucleic acid (dsRNA). The dsRNA can be synthetic, such as, for example, poly I:poly C, poly A:poly U, poly G:poly C, and the like. Likewise, and preferably, the dsRNA can be of natural origin. Among the specific sources of natural dsRNA are virus particles found in certain strains of *Penicillium chrysogenum, Penicillium funiculosum, Penicillium stoloniferum, Aspergillus niger, Aspergillus foetidus,* φ6 bacteriophage, and the like.

A preferred strain useful in the production of dsRNA is *Penicillium chrysogenum*. Methods for producing and isolating dsRNA are well recognized in the literature, see, e.g., U.S. Pat. No. 3,597,318; and U.S. Pat. No. 3,582,469.

The composition of this invention is a complex of dsRNA and tobramycin. The relative amounts of each are defined in terms of the B/P ratios in which B represents moles of tobramycin and P represents moles of dsRNA phosphorus. Although there is no upper limit for the B/P ratio, in order to achieve the desired effectiveness, the ratio must be at least about 1:1.

The preferred B/P ratio is from about 12:1 to about 1:1, and most preferably, is from about 9:1 to about 6:1.

The following represents a general procedure for producing a complex of this invention. Lyophilized dsRNA is dissolved in 0.02M Tris 0.1M NaCl pH 7.0 buffer. The solution is dialyzed overnight against the same buffer system. The procedure uses baked glassware throughout, and all buffers are filtered through a Nalgene 45 micron filter for sterility. Pyrogen-free double distilled water is used for all solutions to minimize any possibility of endotoxin contamination.

The concentration of the dsRNA solution is determined from its UV spectrum on the following basis:

$$44.7 \times OD_{260} = \text{micrograms dsRNA/ml}.$$

For example, for *Penicillium chrysogenum* dsRNA, the moles of RNA phosphorus are determined from the optical density (OD) at 260 nm using an extinction coefficient of 7200. The extinction coefficients of other natural and synthetic double stranded RNA's can be obtained from the literature or determined using standard procedures and this coefficient then used in determining the molar concentration of dsRNA phosphorus.

If appropriate, the dsRNA solution can be diluted with pyrogen-free buffer to facilitate formation of a complex having the desired B/P ratio.

A stock solution of tobramycin is prepared using the same buffer used for the dsRNA solution. The molar concentration of the tobramycin as free base is calculated. This can be determined (a) from its known potency value or (b) from its chemical structure. The pH of the tobramycin stock solution then is carefully adjusted to 7.0 using 1N HCl.

Aliquots of the dsRNA and tobramycin solutions are mixed in amounts to obtain a complex having the desired B/P ratio.

The complex can be used as is in which case it is incubated for approximately one hour before use. Alternatively, the complex can be isolated and reconstituted in another suitable carrier. The complex is stable in any physiologically acceptable carrier, generally in combination with a supporting monovalent ion concentration of about 0.1M buffered to a pH of about 6.8 to about 7.2. Physiological saline in bicarbonate or phosphate buffer is a preferred carrier.

The complexes of this invention have wide applicability. Since dsRNA is rapidly destroyed in human serum due to the presence of degrading RNase, dsRNA in that environ has little or no interferon-inducing capacity or other biological property that is dependent upon the integrity of its native structure. The complexes of this invention, however, exhibit excellent interferon-inducing and macrophage-activation properties even in the presence of dsRNA-degrading RNase. Thus, the complexes of this invention are useful in the induction of interferon, particularly in humans in the presence of human serum RNase.

The complexes of this invention also find particular usefulness in inhibiting the proliferation and migration of tumor cells. Heretofore, it has been recognized that synthetic dsRNA inhibits tumor growth in mice [H. B. Levy, L. W. Law, and A. S. Robson, *Proc. Nat. Acad. Sci.*, 62, 357-361 (1969)]; is active in the treatment of leukemic mice [L. D. Zeleznick, and B. K. Bhuyan, *Proc. Soc. Exp. Biol. Med.*, 130, 126-128 (1969)]; and inhibits chemically-induced tumorigenesis in mouse skin [Gelboin, H. V., and Levy, H. B., *Science*, 167, 205-207 (1970)]. The complexes of this invention exhibit a potentiation of the tumor effect relative to dsRNA alone. This potentiation is wholly unexpected since it exists even in the absence of human serum RNase shown to degrade dsRNA but not the complexes of this invention. Desirably, the complexes of this invention are particularly useful in adjuvant cancer therapy to inhibit metastatic cancer development.

The complexes of this invention can be used in a variety of pharmaceutical compositions and formulations and can be administered by a variety of conventional routes, such as intramuscular, intravenous, subcutaneous, intranasal, topical, and intraperitoneal.

The compositions of this invention can be administered parenterally or intraperitoneally. The pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the complex of this invention in the required amount of the appropriate solvent with various of the other ingredients, as desired.

For more effective distribution, the complex can be incorporated into slow release or targeted delivery systems such as polymer matrices, liposomes, and microspheres.

As noted, the complexes of this invention also can be used topically, for example, for the treatment of warts and other surface viral lesions such as those caused by herpes infection and for the treatment of skin cancers. Thus, the complexes can be formulated as ointments, creams, lotions, and the like.

In formulating an ointment, the complex, for example, is finely dispersed in paraffin. Liquid paraffin, hard paraffin, and wool fat may be included in the ointment base. If a water-miscible ointment base is desired, a polyethylene glycol may be included.

The complex may also be formulated as a cream, which may be an oil-in-water type or a water-in-oil type. Suitable emulsifying agents for the former are sodium, potassium, ammonium and triethanol soaps; polysorbates; and cationic, anionic, and non-ionic emulsifying waxes. Suitable emulsifying agents for the latter type are calcium soaps, wool fat, wool alcohols, beeswax, and certain sorbitan esters. A preservative usually is desirable in a cream, particularly an aqueous cream. Examples of suitable preservatives, alone or in combination, are chlorocresols, p-hydroxybenzoates, and the like.

The complex may be formulated as a lotion by dissolving or dispersing it in an aqueous or oily base. Ethanol and/or glycerin may be included in the aqueous base. Examples of suitable oil bases are castor oil, vegetable oils, and the like. A suitable preservative may be incorporated in the formulation.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Except insofar as any conventional media or agent is incompatible with the compositions of this invention, its use in the therapeutic formulation is contemplated. Supplementary active ingredients can also be incorporated into the pharmaceutical formulations.

It is especially advantageous to formulate parenteral compositions in dosage unit form for ease of administration and uniformity of dosage. Dosage unit form as used herein refers to a physically discrete unit suited as unitary dosages for the subject to be treated. Each unit contains a predetermined quantity of the complex of this invention calculated to produce the desired therapeutic effect in association with the pharmaceutically acceptable carrier. The specific dosage unit form is dictated by and directly dependent upon (a) the unique characteristics of the particular composition and (b) the particular therapeutic effect to be achieved.

In general, the compositions of this invention can be administered to a host in an effective amount as an inducer of interferon or as an adjunct to tumor chemotherapy, tumor radiation therapy, and/or tumor excision. In the case of the latter, the composition can be administered at the same time as such therapy or within an appropriate time prior to or subsequent to such therapy.

As indicated, the compositions can be administered parenterally. Such administration generally will be an amount ranging, for example, from about 5 $\mu$g. to about 500 $\mu$g. dsRNA per kg. of body weight, and preferably, from about 5 $\mu$g. to about 100 $\mu$g. per kg. of body weight, and, most preferably, from about 20 $\mu$g. to about 60 $\mu$g. per kg. of body weight.

The following examples are provided to illustrate the instant invention. They are not intended to be limiting upon the scope thereof.

EXAMPLE 1

Tobramycin-*Penicillium Chrysogenum* dsRNA (PCMdsRNA) Complex, B/P=7.

The absorption spectra of the PCMdsRNA stock was recorded. The concentration of RNA phosphorus was determined using an $\epsilon p$ value of 7200. To 4 ml. of a solution of $1.24 \times 10^{-4}$ mM phosphorus ($OD_{260}=0.895$) PCMdsRNA in 0.02M Tris, 0.1M NaCl, pH 7.0 were added 4 ml. of a solution containing 0.436 mg./ml. tobramycin in the same buffer brought to pH 7.0 with 0.1N HCl. The potency of the tobramycin sample was 0.93 mg. free base/mg. sample. The final concentrations were $4.35 \times 10^{-4}$ mM tobramycin as free base and $6.21 \times 10^{-5}$ mM PCMdsRNA phosphorus which is a B/P of 7.0. The solution was allowed to incubate for 1 hour at room temperature before use.

EXAMPLE 2

Tobramycin-*Penicillium Chrysogenum* dsRNA (PCMdsRNA) Complex, B/P=2

To 4 ml. of a solution of $1.24 \times 10^{-4}$ mM phosphorus ($OD_{260}=0.895$) PCMdsRNA in 0.02 M Tris, 0.1 M NaCl, pH 7.0 were added 4 ml. of a solution containing 0.125 mg./ml. tobramycin in the same buffer brought to a pH of 7.0 with 0.1N HCl. The potency of the tobramycin samples was 0.932 mg. free base/mg. sample. The final concentrations were $0.124 \times 10^{-4}$ mM moles tobramycin as free base and $6.21 \times 10^{-5}$ mM PCMdsRNA phosphorus which is a B/P of 2.0. The solution was allowed to incubate for 1 hour at room temperature before use.

EXAMPLE 3

Tobramycin-Poly I-Poly C Complex, B/P=7.

To 10 mg. of lyophilized salt-free Poly I-Poly C (P. L. Biochemicals, Lot 547261) were added 10 ml. of 0.02M Tris, 0.1M NaCl, pH 7.0 buffer. The samples was equilibrated for 1 hour at 50° C. and allowed to cool slowly overnight to room temperature. An $\epsilon p$ of 5200 was used to determine Poly I-Poly C phosphorus concentration.

To 4 ml. of the Poly I-Poly C duplex solution ($OD_{260}=0.64$, concentration of phosphorus $=1.23 \times 10^{-4}$ mM) were added 4 ml. of a solution containing 0.436 mg./ml. of tobramycin in the same buffer brought to a pH of 7.0 with 0.1N HCl. The potency of the tobramycin was 0.93 mg. free base/mg. sample. The final concentrations were $4.35 \times 10^{-4}$ mM tobramycin as free base and $6.15 \times 10^{-5}$ mM Poly I-Poly C phosphorus which is a P/B of 7.0. The solution was allowed to incubate for 1 hour at room temperature.

The interferon-inducing capacity of the complexes of this invention is demonstrated by a recognized procedure. In this procedure, dsRNA is dissolved in 0.15M saline 0.02M Tris buffer at a concentration suitable for administration, generally about 20 $\mu$g./ml. The dsRNA-tobramycin complex of this invention is prepared by addition to the dsRNA of tobramycin in an amount to produce the desired B/P ratio. The resulting mixture is incubated for about one hour at room temperature to effect optimal tobramycin-dsRNA binding.

Four mice are injected intraperitoneally (i.p.) with the solution (generally 0.5 ml.) containing a total of 10 $\mu$g. of dsRNA whether alone or as the tobramycin-dsRNA complex. Sixteen hours following injection, the mice are bled, and the blood is pooled and centrifuged to obtain the serum. Half-log dilutions of the serum are made using M199 medium, and the separate dilutions (2.5 ml.) are applied to confluent mouse L-cell cultures in Falcon 25 cm.$^2$ tissue culture flasks and allowed to incubate for 20 hours. The cultures then are inoculated with vesicular stomatitis virus in 2.5 ml. of M199 medium at a virus concentration producing 60–100 plaques per flask. After two hours viral adsorption, the fluid is removed, and M199 agar (65%) is applied and allowed to harden. After three days, the flasks are treated with 2% sodium acetate and 3.7% formaldehyde to fix the cells. The plaques are counted, and the amount of interferon is determined on the basis of plaque reduction relative to control plates lacking interferon. One unit of interferon is defined as the reciprocal of the dilution of the interferon solution (mouse serum) that provides 50% inhibition of virus plaque production. The amount of interferon then is calculated by the product of this determination and the total dilution.

The degradative effect of human serum dsRNase on the interferon-inducing capacity of dsRNA or dsRNA-tobramycin is determined by adding human serum to the solution of dsRNA or dsRNA-tobramycin complex. The amount of buffer is appropriately reduced to accomodate the amount of added human serum and to maintain a constant concentration of dsRNA. The resulting mixture is incubated at 37° C. for one hour and then placed in ice. The solutions are used within 15 minutes following removal from the 37° C. bath.

Table I following compares the actions of dsRNA and a composition of this invention in inducing interferon following treatment with human serum.

TABLE I

| Compound[a] | Human Serum[b] | Interferon, units |
| --- | --- | --- |
| tobramycin | Yes | 35 |
| dsRNA | No | 1050 |
| dsRNA + tobramycin | No | 3200 |
| dsRNA | Yes | 447 |
| dsRNA + tobramycin | Yes | 3470 |

[a]Dose—0.5 ml.; dsRNA concentration—20 µg./ml.; tobramycin concentration—14.5 µg./ml. (B/P = 1).
[b]1.2 µl./ml. of sample.

Table II following shows the effects on interferon induction of varying (a) the B/P ratio of tobramycin and dsRNA and (b) the concentration of human serum.

TABLE II

| Compound[a] | B/P | Human serum, ml. per each 3 ml. sample | Interferon, units |
| --- | --- | --- | --- |
| Control (Buffer) | — | — | <31 |
| dsRNA | — | — | 3160 |
| dsRNA | — | 1.0 | <31 |
| dsRNA-tobramycin | 4 | — | 2570 |
| dsRNA-tobramycin | 4 | 1.0 | 1479 |
| dsRNA-tobramycin | 4 | 2.0 | 1230 |
| dsRNA-tobramycin | 4 | 2.5 | 346 |
| dsRNA-tobramycin | 6 | 1.0 | 2042 |
| dsRNA-tobramycin | 6 | 2.0 | 891 |
| dsRNA-tobramycin | 6 | 2.5 | 447 |

[a]Dose—0.5 ml.; dsRNA concentration—20 µg./ml.

Table III shows the effect on interferon induction after challenge with 83% human serum (2.5 ml. per 3.0 ml. sample) of various tobramycin-dsRNA B/P ratios.

TABLE III

| Tobramycin-dsRNA, B/P | Interferon Induced, Units |
| --- | --- |
| 4 | 110 |
| 8 | 234 |
| 12 | 310 |
| 16 | 310 |
| 20 | 417 |
| 40 | 316 |
| 16[a] | 1667 |

[a]Run without human serum challenge

The activity of the complexes of this invention on macrophage activation has been determined according to a recognized procedure. In this procedure, peritoneal macrophages were harvested after 5 days from composition-treated mice by peritoneal lavage and purified by adherence on plastic. Approximately $4 \times 10^5$ macrophages in 16 mm. wells were overlaid with $4 \times 10^4$ P815 cells contained in 2 ml. of Roswell Park Memorial Institute 1640 Medium supplemented with 20% fetal calf serum. All cultures were maintained in a humidified, 5% $CO_2$-in-air incubator at 37° C., and cytotoxicity was assessed at 48 hours on the basis of viable cell counts in a hemocytometer. Triplicate cultures were maintained for each group; the mean cell count and standard error (S.E.) were calculated. Under these conditions, peritoneal macrophages from normal BALB/C mice treated with tris-buffered saline did not affect the growth of P815 target cells, as measured both by viable cell number and by DNA synthesis of the leukemia cells. The ratio of macrophages to target cells was approximately 10:1 at the beginning of each experiment. The percentage of growth inhibition of P815 cells due to composition-mediated macrophage activation was calculated by comparison to that of P815 cells grown in the presence of macrophages from buffer-treated animals. The results are provided in Table IV following:

TABLE IV

In Vivo Macrophage Activation Using dsRNA-Tobramycin Complex

| Compound | Amount of Compound[a] | Amount of Human Serum | Percent Macrophage Cytotoxicity Expt. 1 | Percent Macrophage Cytotoxicity Expt. 2 |
| --- | --- | --- | --- | --- |
| dsRNA | 10 µg. | — | 91 | 70 |
| dsRNA | 10 µg. | 0.002 ml. | 78 | 58 |
| dsRNA | 10 µg. | 0.42 ml. | 30 | 6 |
| dsRNA-tobramycin | 10 µg. + 100 µg. | — | 89 | 81 |
| dsRNA-tobramycin | 10 µg. + 100 µg. | 0.42 ml. | 74 | 69 |
| Tobramycin | 100 µg. | — | −1 | 0 |
| None | — | — | 0 | 0 |

[a]A total of 0.5 ml. of incubation mixture was given i.p. 5 days prior to harvest of peritoneal macrophages. Dose given is the amount injected per mouse.

The activity of the complexes of this invention against the effects of tumor cell metastasis is demonstrated using Madison (M109) lung carcinoma, a highly refractory tumor system to conventional cytoreductive therapy [Marks et al., *Cancer Treatment Reports* 61, 1459–1470 (1977)]. This carcinoma can be carried as a transplantable line in syngeneic BALB/C mice. The tumor line is available from the tumor bank at Mason Research Institute.

In conducting tumor metastasis studies, a subcutaneously-grown tumor is aseptically excised, minced using a scissors, and gently trypsinized at room temperature to obtain a single cell suspension. The cells are suspended in RPMI-1640 medium (M.A. Bioproducts, Walkersville, Md.). Viable M109 cells are determined by trypan blue exclusion, and the cell concentration is determined using a hemocytometer. The cell concentration is adjusted to $1 \times 10^5$ viable cells per ml. of medium. The M109 cell-containing medium is injected into normal, male BALB/C mice in an amount providing the desired number of viable cells. Test compositions are administered intraperitoneally (i.p.) to randomized groups of ten mice each two days prior to tumor cell inoculation if the latter is intravenous (i.v.) and five days after tumor cell inoculation if the latter is subcutaneous (s.c.). Controls receive mock injections of 0.5 ml. carrier. Mortality is monitored to determine percent increased life span (ILS) relative to control, and the median survival time (MST) for each group is determined. Both are calculated from the time of tumor cell administration.

The following Table V provides results using a composition of this invention prepared from tobramycin and *P. chrysogenum*-derived dsRNA. In Experiments 1 and 2, $1 \times 10^4$ M109 cells were administered i.v. two days after administering test compound, and, in Experiment 3, $1 \times 10^5$ M109 cells were administered s.c. five days prior to administering test compound.

TABLE V

| Compound | A-mount | Expt. 1 MST, days | Expt. 1 ILS, % | Expt. 2 MST, days | Expt. 2 ILS, % | Expt. 3 MST, days | Expt. 3 ILS, % |
| --- | --- | --- | --- | --- | --- | --- | --- |
| Control | 0.5 ml | 11 | 0 | 25 | 0 | 31 | 0 |
| Tobramycin | —[a] | 11 | 0 | 26 | 4 | 29 | −6 |
| dsRNA | —[b] | 14 | 27 | 29 | 16 | 39 | 26 |
| Tobramycin-dsRNA | —[c] | 16 | 45 | 49 | 96 | 51 | 65 |

[a]Expt. 1—5.1 mg./kg.; Expts. 2 and 3—5.5 mg./kg.
[b]Expt. 1—0.52 mg./kg.; Expts. 2 and 3—0.53 mg/kg.
[c]Composition (B/P = 7) contains those amounts of tobramycin and dsRNA as were used separately.

Table VI following shows the effectiveness of compositions of this invention using both natural (*P. chrysogenum*-derived) and synthetic dsRNA.

TABLE VI

| Compound (Day −2; i.p.) | Dose, μg. | MST, days | ILS, % |
| --- | --- | --- | --- |
| Control | — | 47 | 0 |
| Tobramycin | 197 | 50 | 6 |
| dsRNA | 10.1 | 56 | 19 |
| dsRNA-Tobramycin | 10.1 + 197 | 66 | 40 |
| poly I:poly C | 10.1 | 65 | 38 |
| poly I:poly C-tobramycin | 10.1 + 197 | 77 | 64 |

Table VII demonstrates the effect of a variety of B/P ratios of tobramycin and *P. chrysogenum*-derived dsRNA on anti-tumor activity.

TABLE VII

| Compound[a] (Day −2; i.p.) | Dose, μg. | B/P | MST, days | ILS, % |
| --- | --- | --- | --- | --- |
| Control | — | | 34.5 | 0.0 |
| dsRNA | 10 | | 37.5 | 8.7 |
| dsRNA-tobramycin | 10 + 101.5 | 7 | 45.5 | 31.9 |
| dsRNA-tobramycin | 10 + 14.5 | 1 | 42.5 | 23.2 |
| dsRNA-tobramycin | 10 + 1.4 | 0.1 | 35.0 | 1.4 |
| tobramycin | 101.5 | | 34.5 | 0.0 |
| tobramycin | 14.5 | | 37.5 | 8.7 |
| tobramycin | 1.4 | | 37.5 | 8.7 |

[a]Mice received 2 × 10$^4$ monodisperse M109 cells i.v. on Day 0.

Table VIII provides a dose response of the anti-tumor activity of a composition of tobramycin and *P. chrysogenum*-derived dsRNA having a B/P of 7.

TABLE VIII

| Compound[a] (Day −2; i.p.) | Dose, μg. | MST, days | ILS, % |
| --- | --- | --- | --- |
| Control | — | 32 | — |
| dsRNA | 40 | 34 | 7 |
| dsRNA | 10.45 | 37 | 14 |
| dsRNA | 2.5 | 34 | 7 |
| dsRNA-tobramycin | 40 + 405 | 45 | 41 |
| dsRNA-tobramycin | 10 + 101.5 | 48 | 50 |
| dsRNA-tobramycin | 2.5 + 25 | 35 | 9 |
| Tobramycin | 405 | 32 | 0 |

[a]Mice received 2 × 10$^4$ monodisperse M109 cells i.v. on Day 0.

We claim:

1. A complex comprising (a) natural or synthetic double stranded RNA and (b) tobramycin in a molar ratio of tobramycin to double stranded RNA phosphorus of at least about 1:1.

2. Complex of claim 1, in which the double stranded RNA is of natural origin.

3. Complex of claim 2, in which the double stranded RNA source is *Penicillium chrysogenum*.

4. Complex of claim 3, in which the molar ratio of tobramycin to double stranded RNA phosphorus is from about 12:1 to about 1:1.

5. Complex of claim 3, in which the molar ratio of tobramycin to double stranded RNA phosphorus is from about 9:1 to about 6:1.

6. A pharmaceutical composition suitable for inducing interferon comprising in combination with a pharmaceutically acceptable carrier an interferon-inducing amount of a complex of (a) natural or synthetic double stranded RNA and (b) tobramycin in a molar ratio of tobramycin to double stranded RNA phosphorus of at least about 1:1.

7. Composition of claim 6, in which the double stranded RNA is of natural origin.

8. Composition of claim 7, in which the double stranded RNA source is *Penicillium chrysogenum*.

9. Composition of claim 8, in which the molar ratio of tobramycin to double stranded RNA phosphorus is from about 12:1 to about 1:1.

10. Composition of claim 8, in which the molar ratio of tobramycin to double stranded RNA phosphorus is from about 9:1 to about 6:1.

* * * * *